US010136211B2

(12) United States Patent
Jenkins

(10) Patent No.: US 10,136,211 B2
(45) Date of Patent: Nov. 20, 2018

(54) METHOD OF CUSTOMIZING SPEAKER FOR HEARING PROTECTION EARCUP

(71) Applicant: Honeywell International Inc., Morristown, NJ (US)

(72) Inventor: John Jenkins, San Diego, CA (US)

(73) Assignee: Honeywell International Inc., Morris Plains, NJ (US)

( * ) Notice: Subject to any disclaimer, the term of this patent is extended or adjusted under 35 U.S.C. 154(b) by 255 days.

(21) Appl. No.: 14/573,172

(22) Filed: Dec. 17, 2014

(65) Prior Publication Data

US 2016/0175155 A1   Jun. 23, 2016

(51) Int. Cl.
*A61F 11/06* (2006.01)
*H04R 1/10* (2006.01)
*A61F 11/14* (2006.01)

(52) U.S. Cl.
CPC ............ *H04R 1/1083* (2013.01); *A61F 11/14* (2013.01)

(58) Field of Classification Search
CPC .... G10K 11/175; H04R 27/00; H04R 1/1083; A61F 11/14
See application file for complete search history.

(56) References Cited

U.S. PATENT DOCUMENTS

| 8,582,796 B2 * | 11/2013 | Kimura | H04R 1/1008 2/209 |
| 2003/0138112 A1 * | 7/2003 | Doy | H03F 3/005 381/74 |
| 2008/0154404 A1 * | 6/2008 | Kedem | G11B 25/10 700/94 |
| 2008/0240468 A1 * | 10/2008 | Adam | H01R 4/2408 381/120 |
| 2010/0215198 A1 * | 8/2010 | Ngia | H04R 1/1016 381/309 |
| 2010/0296667 A1 * | 11/2010 | Parkins | H04M 1/05 381/74 |
| 2012/0008793 A1 * | 1/2012 | Knox | H04R 1/10 381/74 |
| 2012/0243700 A1 * | 9/2012 | Jenkins | H04R 1/1083 381/72 |
| 2015/0117660 A1 * | 4/2015 | Fletcher | G10K 11/178 381/72 |

FOREIGN PATENT DOCUMENTS

| CN | 103237277 A | 8/2013 |
| CN | 203279137 U | 11/2013 |

\* cited by examiner

*Primary Examiner* — Simon King
(74) *Attorney, Agent, or Firm* — Wick Phillips Gould & Martin, LLP

(57) ABSTRACT

Embodiments relate generally to methods for customizing speakers in hearing protection earcups in conjunction with an amplifier so that the maximum speaker output may be capped, for example to acceptable OSHA or other such standards. By customizing such speaker(s), the maximum speaker output may be set precisely at the desired cap level. Thus, hearing may be protected, while also ensuring that maximum speaker output will not undershoot the desired cap level (which might negatively affect performance).

19 Claims, 1 Drawing Sheet

METHOD OF CUSTOMIZING SPEAKER FOR HEARING PROTECTION EARCUP

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Some safety equipment hearing protection devices, such as passive noise reduction earmuffs, also have speakers included therein (for example, for communication and/or entertainment functions). However, it makes no sense to protect a user from external noise which might cause hearing damage or loss, while simultaneously allowing the speakers to broadcast at such a high sound level that they may cause damage to the user's hearing. Thus, there may be a need to limit speaker output to safe levels.

Current solutions for this type of issue typically rely on adding resistors to the circuitry (for example, between the amplifier and the speaker). This approach is often used to account for the pre-set resistance levels of off-the-shelf speakers, which have ratings that are not mated to any specific amplifier's output. But, this approach typically may not allow for precise capping of the sound emitted by the speaker. Additionally, this type of approach may take up more space in the earcup of the earmuff, thereby inadvertently impacting the noise reduction rating of the earcup (which, after all, is typically the most important aspect of a hearing protection earcup). And clearly, such an approach may also complicate manufacturing with additional steps, and may lead to increased scrap rates and field failures. The presently disclosed embodiments relate to improved hearing protection earcups, for example having customized speakers which may be specifically mated to match amplifier output, and may address one or more of the issues of the current approach.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
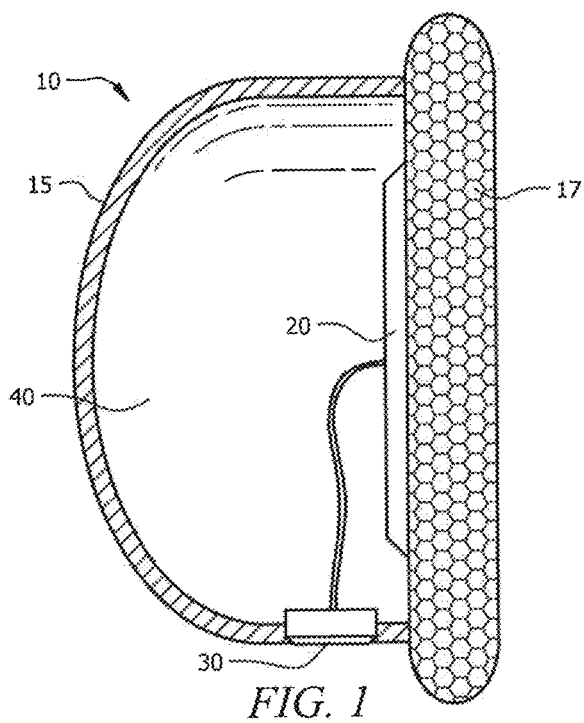
FIG. 1 illustrates schematically a cross-section of an exemplary embodiment of an earcup.
Figure 2:
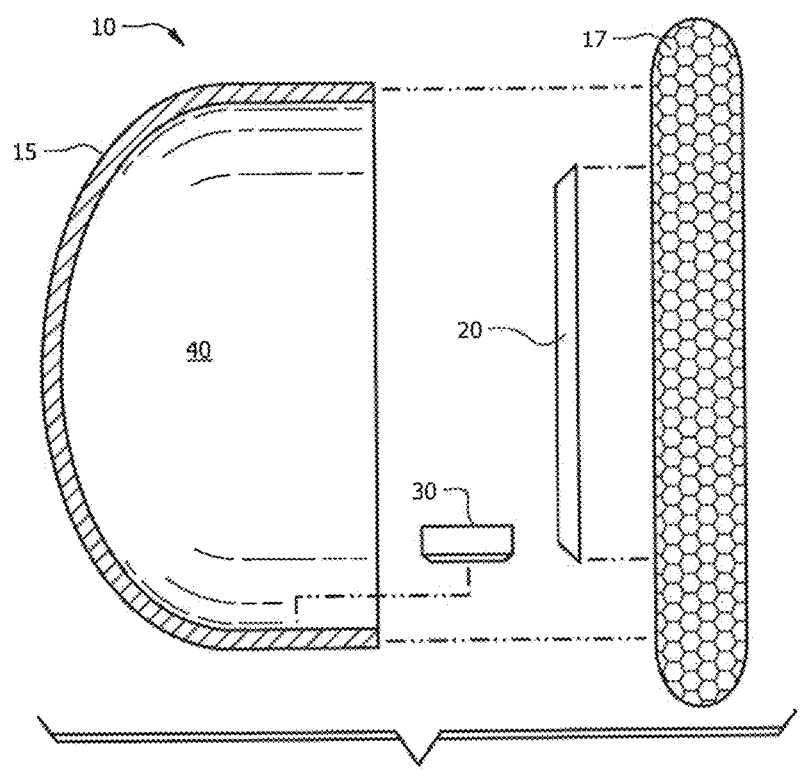
FIG. 2 illustrates schematically an exploded view of the elements of the exemplary embodiment of FIG. 1.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Disclosed embodiments typically relate to hearing protection earmuffs, which generally might have two earcups providing passive noise reduction (e.g. an effective NRR (Noise Reduction Rating) to protect a user from a damaging external noise environment). More specifically, disclosed embodiments relate to such hearing protection earcups having a speaker therein (for example, for use in conjunction with communications gear and/or entertainment equipment (such as a music player)). This is safety equipment, however, so it may be important to ensure that the earcup's NRR is not unduly affected by the speaker (e.g. the NRR rating of the earcup typically should still be sufficiently high to protect the user), and to ensure that the speaker itself does not cause any hearing damage to the user. Disclosed embodiments might typically achieve such goals by customizing a speaker for use in conjunction with an amplifier, to precisely limit or cap the maximum speaker output at the desired level. This may offer effective protection (by, for example, ensuring that the speaker is unlikely to cause damage and by ensuring that the electrical elements do not impinge on the NRR of the earcup), while also ensuring that the maximum speaker output does not undershoot the desired cap level (which, for example, might negatively impact speaker performance). Thus, improved design processes may lead to improved products, as persons of skill will understand in light of the disclosure below.

Disclosed method embodiments (for customizing a speaker in a hearing protection earcup) typically might comprise the following steps: selecting an amplifier; selecting a speaker, and/or placing the speaker and the amplifier in a hearing protection earcup, wherein the combination of the speaker and the amplifier maximum output provides a maximum speaker output which is limited/set to (typically precisely/exactly) a desired cap level (for example, the maximum legally allowed continuous noise exposure level, for example for an 8 hour period). For example, in the United States the maximum legally allowed continuous noise exposure level might be the limit set by OSHA (e.g. Occupational Safety Health Administration) or NIOSH (e.g. National Institute of Occupational Safety and Health). So under current U.S. government regulations, the speaker output might be limited to a level of about 82-85 dB (for example, preferably 82 dB or 85 dB). And typically, the earcup would provide effective noise reduction for a user, for example having at least 20 NRR (or alternatively, 20-30 NRR, 25 NRR, or 25-30 NRR), despite the presence of electronics such as the speaker and the amplifier within the earcup. Typical amplifier output might be from about 100-1000 milliamps.

Typically, selecting a speaker would comprise accounting for resonance of the earcup. For example, earcup resonance might be measured using attenuation measurements and finding resonance spikes in the attenuation curve. The speaker could then be chosen to have resonance that does not match (for example, far away from) the resonance of the earcup (for example, the speaker could be selected to have resonance as far away from the resonance of the earcup as possible). So in some embodiments (for example, having an amplifier with 100 milliamps continuous output with maximum output of 1000 milliamps), the selected speaker may have electric resistance between 16 and 32 Ohms (or alternatively from about 22 to 23 Ohms). Also, the earcup of disclosed embodiments typically would not contain any additional electrical resistance elements (for example, in line electrically with the speaker/between the amplifier and the speaker). Rather, selecting a speaker would comprise designing/customizing/providing the speaker with resistance customized so the maximum speaker output does not overshoot and/or undershoot the (legal) limit for exposure on its own (e.g. when the amplifier is directly connected to the speaker, without any additional resistance elements). So in such embodiments, the speaker would not be an off-the-shelf speaker, but rather would be custom designed with specific resistance (e.g. Ohm rating) matching the specific amplifier (as discussed above, to ensure that (without any other resistance elements) when the amplifier drives the speaker to maximum speaker output, the maximum speaker output would be limited/capped, for example precisely at the maximum legally allowed continuous noise exposure level).

Since embodiments relate to passive noise reduction earcups for hearing protection, design of the earcups to provide effective passive NRR may often be quite important (and indeed may often be the driving factor for the design). Indeed, there may be synergistic effect between the customization of the speaker and the NRR design of the earcup itself. For example, the earcup may be designed/constructed to maximize hearing protection without concern for speaker issues (since the speaker can later he selected precisely to account for earcup resonance, for example). This is quite different from standard designs, in which earcup resonance may affect speaker issues (thereby limiting the earcup NRR design, for example). So in some embodiments, the method might further comprise selecting/designing an earcup to maximize hearing protection (or achieve a target hearing protection level or NRR) without concern for the speaker (since the speaker can later be selected precisely to account for any resulting earcup resonance). In other words, speaker design accounts for any resonance of the earcup, so any such resonance of the earcup will not cause the maximum speaker output to vary (e.g. exceed) from the desired cap level/precise maximum legally allowed noise exposure level. Selecting/designing an earcup may further comprise maximizing interior airspace while maintaining an acceptable low (exterior) profile, managing the weight of the hearing protection device/earcup so that it remains comfortable to the user, and/or selecting a clamping force (for example, for the headband linking the two earcups) sufficient to maintain an airtight seal between the exterior environment airspace and the interior airspace of the earcups while also remaining sufficiently comfortable for a user to wear over long periods. So for example, the earcup might typically have 100,000 to 300,000 cubic millimeters air space volume (for example, about 220,000 cubic millimeters in some embodiments) behind the speaker (to help ensure effective passive NRR). Regardless, the earcup typically is designed to provide adequate/effective hearing protection from external noise environments (for example noise environments in a range of 90-110 dB, such as airports, construction sites, or industrial plants).

Typically, the speaker would be located at or near the inner surface of the opening of the earcup (for example, just inside the earcup and facing the user's ear canal, below the most exterior part of the cushion), and the amplifier would be located closer to the exterior wall of the earcup shell (for example located on a circuit board that is mounted as far away from the user and exterior elements as possible in the earcup) (e.g. so the method might comprise placing the speaker and amplifier in the earcup in the desired location). Additionally, method embodiments might include electrically connecting the amplifier o the speaker (e.g. so that the speaker would be driven by the amplifier). And typically, there would be no other/additional resistance elements located electrically between the amplifier and the speaker (such that the amplifier and speaker would be directly coupled to each other electrically, without any intervening resistive elements). In other words, in some embodiments, there would be no additional resistance elements within the earcup. Conventionally, this type of electrical alignment did not occur, since other electrical resistance elements would typically be needed to ensure that the amplifier could not drive the speaker above the desired maximum speaker output (e.g, cap level). But with the speaker being customized to the specific amplifier, additional resistance elements are unnecessary and, in fact, typically would not be used (thereby freeing additional air space volume in the earcup for NRR purposes).

In some embodiments, the earcup might further comprise foam, for example located in at least a portion of the air space volume (e.g. behind the electrical components/elements such as the speaker and/or amplifier) to further improve passive NRR characteristics of the earcup. Thus, the method embodiment may include placing foam within the earcup. For example, foam may typically range from 1 mm up to the open volume of the earcup. And typically reticulated and/or non-reticulated foam might be used (for example, filling the open volume space of the interior of the cup). Embodiments might also typically include a retaining element, for example operable to hold the speaker in place in the earcup at the desired location. So for example, speakers may be mounted firmly to the earcup, for example using a molded in boss and fixture which may be attached to the rim of the cup (thus suspending the speaker so they do not directly touch the cup). Related method embodiments might include using the retaining element to fix the location of the speaker in the earcup. And in some embodiments, the earcup may also comprise a sealing section, for example a cushion located about edge of the cup, which might be attached thereto (and may be operable to improve the seal of the earcup on the user's head around the ear, for example providing an airtight seal).

Such method embodiments (of the sort described above for example) typically would result in device embodiments which may provide improved features. For example, a hearing protection device embodiment might comprise: an earcup (for example, providing at least NRR of 20 or NRR in a range of 20-30 (or 25-30) and/or at least 100,000 cubic millimeters (or 100,000-300,000 cubic millimeters) of air space volume behind the speaker, etc.); a speaker (located within the earcup); and an amplifier (located within the earcup and in electrical connection with the speaker (e.g. wherein the amplifier drives the speaker)); wherein the speaker has electrical resistance, and the speaker and amplifier combined are operable to provide a maximum speaker output which is limited (e.g. capped) typically precisely/ exactly to a desired cap level (for example, the maximum legally allowed continuous noise exposure level, for example for an 8 hour period). For example, in the United States the maximum legally allowed continuous noise exposure level might be the limit set by OSHA or NIOSH (e.g. National Institute of Occupational Safety and Health). So under current U.S. government regulations, the speaker output might be limited to a level of about 82-95 dB, 82-85 dB, or 85-90 dB (for example, preferably 82 dB or 85 dB).

Typically, the resonance of the earcup is accounted for when capping the maximum speaker output (e.g. the combined output of the speaker and the amplifier). In other words, the resonance of the earcup should not cause the maximum speaker output to vary from the precise/exact desired cap level (e.g. the maximum legally allowed continuous noise exposure). So, the speaker of disclosed embodiments typically would not be an off-the-shelf speaker, but rather would be customized in design with precise resistance for use with the specific amplifier, to result in a precise maximum speaker output which accounts for any earcup resonance. And typically, the earcup would not have any additional electrical resistance elements (e.g. between the amplifier and the speaker). So, disclosed speaker embodiments may have an electrical resistance of between 16-32 Ohms (e.g. in a range from 16-32 Ohms but excluding the end points, so that the customized speaker clearly differs from available off-the-shelf speakers). In some embodiments, speaker resistance might range from about 22-23 Ohms (e.g. including the end points of the range).

FIG. 1 illustrates an exemplary passive hearing protection device (e.g. earmuff earcup) embodiment 10. For example, in FIG. 1 the speaker 20 and amplifier 30 are located within the earcup 15 (e.g. the sealing element or hollow shell body for enclosing a user's ear to shield the ear from external noise environment). More specifically, the speaker 20 of FIG. 1 is located in proximity to the inner opening of the earcup shell (e.g. the speaker might not be spaced back (significantly) from the opening of the cup). The earcup 15 of FIG. 1 is designed to provide effective hearing protection (for potentially damaging noise environments), and thus has an air space volume 40 located behind the speaker 20. In FIG. 1, the air space volume 40 would typically be about 100,000-300,000 cubic millimeters, and the earcup 15 would typically provide 20-30 or 25-30 NRR. Earcup embodiments might further comprise additional elements, such as foam, a retaining element (for holding speaker in place within the earcup, for example proximate to the inner surface that would face the user), a sealing section (or cushion, for example located about the edge of the cup, as shown for example as 17 in FIG. 1), etc.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should he understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented. And logic flows for methods do not necessarily require the particular order shown, or sequential order, to achieve desirable results. Other steps may be provided, or steps may be eliminated, from the described flows/methods, and other components may be added to, or removed from, the described devices/systems. So, other embodiments may be within the scope of the following claims.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method comprising:
selecting an amplifier with a maximum output;
selecting a speaker with respect to tile selected amplifier, wherein the combination of the speaker and the selected amplifier maximum output provides a maximum speaker output which is precisely limited to a desired cap level without undershooting the desired cap level;
electrically coupling the amplifier directly to the speaker; and
placing the speaker and the amplifier in a hearing protection earcup, wherein the earcup provides a range of 20-30 noise reduction rating (NRR) and has between 100,000 to 300,000 cubic millimeters of air space volume behind the speaker, wherein the air space volume behind the speaker is configured to ensure effective passive NRR.

2. The method of claim 1 wherein the desired cap level is the maximum legally allowed continuous noise exposure.

3. The method of claim wherein the maximum speaker output is limited to 85dB.

4. The method of claim I, wherein the maximum speaker output is limited to precisely 85dB.

5. The method of claim 1, wherein the earcup provides 25-30 noise reduction rating (NRR).

6. The method of claim 1, wherein the selected speaker has resistance between 16 and 32 Ohms.

7. The method of claim 1, wherein the selected speaker has resistance from about 22-23 Ohms.

8. The method of claim 1, wherein selecting a speaker comprises accounting for resonance of the earcup.

9. The method of claim 1, wherein there are no additional electrical resistance elements between the amplifier and the speaker.

10. The method of claim 1,, wherein the speaker has internal electrical resistance, and selecting a speaker comprises designing the speaker with resistance customized so the maximum speaker output does not overshoot or undershoot the desired cap level, and wherein the amplifier is coupled to the speaker without any electrical elements therebetween.

11. A hearing protection device comprising:
an earcup operable to provide hearing protection from an external noise environment;
a speaker within the earcup, wherein the earcup has between 100,000 to 300,000 cubic millimeters of air space volume behind the speaker, wherein the air space volume behind the speaker is configured to ensure effective passive NRR; and
an amplifier in direct electrical connection with the speaker, wherein the amplifier drives the speaker;
wherein the speaker has electrical resistance, and the speaker and amplifier combined are operable to provide a maximum speaker output which is limited to precisely a desired cap level.

12. The device of claim 11, wherein the desired cap level is the maximum legally allowed continuous noise exposure.

13. The device of claim 11, wherein the desired cap level for maximum speaker output is in a range from about 82-85 dB.

14. The device of claim 11, wherein the earcup provides 20-30 noise reduction rating (NRR).

15. The device of claim 11, wherein resonance of the earcup will not cause the maximum speaker output to vary from the desired cap level.

16. The device of claim 11, wherein the speaker is not an off-the-shelf speaker, but rather is customized in design with precise resistance for use with the specific amplifier, to result in the maximum speaker output precisely matching the desired cap level.

17. The device of claim 11, wherein the speaker has an electrical resistance of between 16-32 Ohms.

18. The device of claim 11, wherein the speaker has an electrical resistance ranging from about 22-23 Ohms.

19. The device of claim 11, wherein there are no additional electrical resistance elements between the amplifier and the speaker.

* * * * *